US010433813B2

United States Patent
Takimoto

(10) Patent No.: US 10,433,813 B2
(45) Date of Patent: Oct. 8, 2019

(54) ULTRASONIC DIAGNOSTIC APPARATUS

(71) Applicant: Toshiba Medical Systems Corporation, Otawara-shi (JP)

(72) Inventor: Masao Takimoto, Otawara (JP)

(73) Assignee: Canon Medical Systems Corporation, Otawara-shi (JP)

(*) Notice: Subject to any disclaimer, the term of this patent is extended or adjusted under 35 U.S.C. 154(b) by 0 days.

(21) Appl. No.: 14/834,492

(22) Filed: Aug. 25, 2015

(65) Prior Publication Data

US 2015/0359506 A1  Dec. 17, 2015

Related U.S. Application Data

(63) Continuation of application No. PCT/JP2014/054707, filed on Feb. 26, 2014.

(30) Foreign Application Priority Data

Feb. 26, 2013  (JP) ................................. 2013-036021

(51) Int. Cl.
*A61B 8/06* (2006.01)
*A61B 8/08* (2006.01)
(Continued)

(52) U.S. Cl.
CPC .............. *A61B 8/06* (2013.01); *A61B 5/0402* (2013.01); *A61B 5/7289* (2013.01); *A61B 8/14* (2013.01);
(Continued)

(58) Field of Classification Search
CPC ....... A61B 8/06; A61B 5/0402; A61B 5/7289; A61B 8/14; A61B 8/463; A61B 8/488;
(Continued)

(56) References Cited

U.S. PATENT DOCUMENTS 5,622,174 A * 4/1997 Yamazaki .................... 600/441
6,364,835 B1 * 4/2002 Hossack et al. .............. 600/443
(Continued)

FOREIGN PATENT DOCUMENTS

CN  1549933 A  11/2004
CN  1636519 A  7/2005
(Continued)

OTHER PUBLICATIONS

Office Action dated Sep. 23, 2016, in Chinese Patent Application No. 201480010531.7.
(Continued)

*Primary Examiner* — Lynsey C Eiseman
*Assistant Examiner* — Jessandra F Hough
(74) *Attorney, Agent, or Firm* — Oblon, McClelland, Maier & Neustadt, L.L.P.

(57) ABSTRACT

According to one embodiment, there is provided an ultrasonic diagnostic apparatus which comprises data processing circuitry, a display, input interface circuitry and system control circuitry. The data processing circuitry generates at least B-mode data and Doppler spectral data. The display displays images based on the B-mode data and the Doppler spectral data that have been generated by the data processing circuitry. The input interface circuitry inputs one of an instruction to transit to a mode of the Doppler spectral data and an operation to a range gate. The system control circuitry changes a display form of the Doppler spectral data displayed on the display based on the Doppler spectral data generated in a predetermined time after the input in response to the input to the input interface circuitry.

6 Claims, 3 Drawing Sheets

(51) Int. Cl.
*A61B 5/0402* (2006.01)
*A61B 8/14* (2006.01)
*A61B 8/00* (2006.01)
*G01S 7/52* (2006.01)
*G01S 15/89* (2006.01)
*A61B 5/00* (2006.01)
*A61B 5/0245* (2006.01)

(52) U.S. Cl.
CPC .............. *A61B 8/463* (2013.01); *A61B 8/488* (2013.01); *A61B 8/5284* (2013.01); *G01S 7/52066* (2013.01); *G01S 7/52071* (2013.01); *G01S 15/8986* (2013.01); *G01S 15/8988* (2013.01); *A61B 5/0245* (2013.01); *A61B 5/742* (2013.01); *A61B 5/7475* (2013.01); *A61B 8/486* (2013.01)

(58) Field of Classification Search
CPC ..... A61B 8/5284; A61B 5/0245; A61B 5/742; A61B 5/7475; A61B 8/486; G01S 7/52066; G01S 7/52071; G01S 15/8986; G01S 15/8988
See application file for complete search history.

(56) References Cited

U.S. PATENT DOCUMENTS

| | | | | |
|---|---|---|---|---|
| 6,450,959 | B1* | 9/2002 | Mo et al. .................... | 600/441 |
| 6,554,770 | B1 | 4/2003 | Sumanaweera et al. | |
| 7,837,624 | B1* | 11/2010 | Hossack et al. .............. | 600/443 |
| 8,979,760 | B2* | 3/2015 | Zhang .................... | A61B 8/06 |
| | | | | 600/453 |
| 2002/0120195 | A1* | 8/2002 | Hossack et al. .............. | 600/443 |
| 2003/0045797 | A1 | 3/2003 | Christopher et al. | |
| 2004/0102706 | A1 | 5/2004 | Christopher et al. | |
| 2005/0203401 | A1* | 9/2005 | Takimoto .................... | 600/441 |
| 2006/0025684 | A1* | 2/2006 | Quistgaard et al. .......... | 600/441 |
| 2007/0167790 | A1* | 7/2007 | Kim et al. .................... | 600/454 |
| 2010/0094100 | A1* | 4/2010 | Fujii ...................... | A61B 8/00 |
| | | | | 600/300 |
| 2012/0059262 | A1* | 3/2012 | Clark ........................... | 600/440 |
| 2012/0116224 | A1* | 5/2012 | Haugen et al. ............... | 600/443 |
| 2012/0157845 | A1* | 6/2012 | Rabben et al. ............... | 600/443 |
| 2014/0125691 | A1* | 5/2014 | Lysyansky .......... | A61B 8/0883 |
| | | | | 345/619 |
| 2014/0213905 | A1* | 7/2014 | Saad ................... | G01S 15/8984 |
| | | | | 600/441 |

FOREIGN PATENT DOCUMENTS

| | | |
|---|---|---|
| CN | 102414575 A | 4/2012 |
| JP | 02-309934 A | 12/1990 |
| JP | 2005-500888 A | 1/2005 |
| JP | 2010-088943 A | 4/2010 |
| JP | 4538091 B2 | 6/2010 |
| JP | 2013-027454 A | 2/2013 |

OTHER PUBLICATIONS

International Search Report dated Apr. 1, 2014 for PCT/JP2014/054707 Filed on Feb. 26, 2014 (English Language).
International Written Opinion dated Apr. 1, 2014 for PCT/JP2014/054707 Filed on Feb. 26, 2014.

* cited by examiner

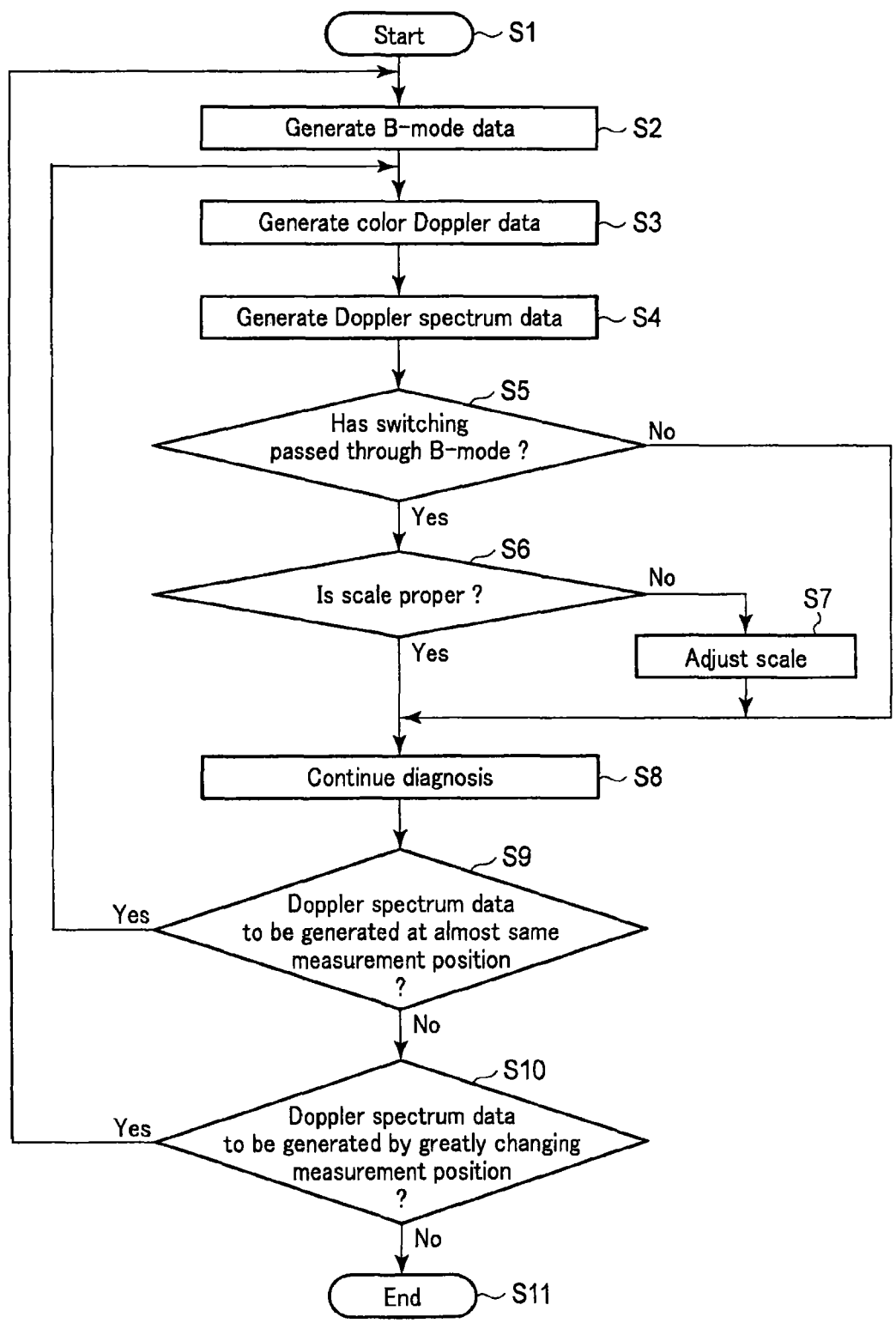
F I G. 2

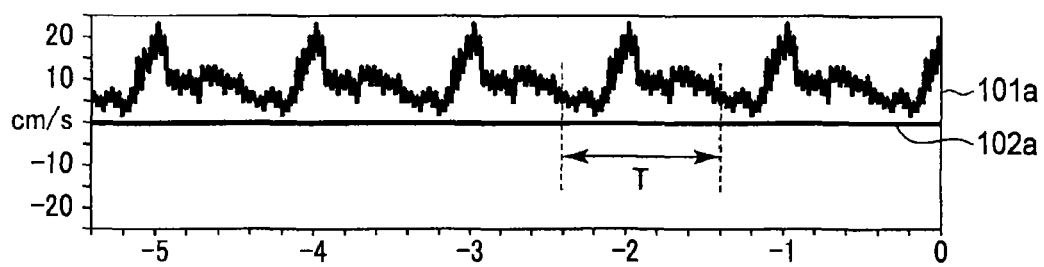
F I G. 3
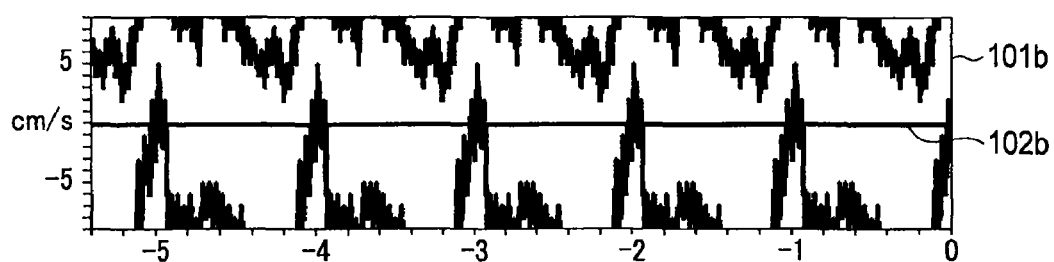
F I G. 4
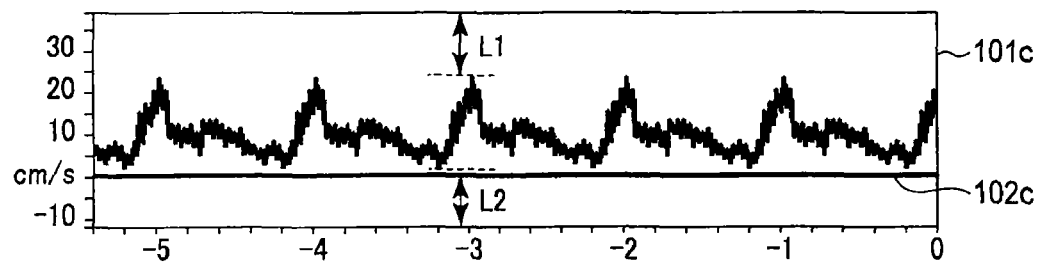
F I G. 5

ULTRASONIC DIAGNOSTIC APPARATUS

CROSS-REFERENCE TO RELATED APPLICATIONS

This application is a Continuation Application of PCT Application No. PCT/JP2014/054707, filed Feb. 26, 2014 and based upon and claims the benefit of priority from the Japanese Patent Application No. 2013-036021, filed Feb. 26, 2013, the entire contents of all of which are incorporated herein by reference.

FIELD

Embodiments described herein relate generally to an ultrasonic diagnostic apparatus.

BACKGROUND

There is a technique of displaying blood flow information of a patient as an image by a so-called ultrasonic Doppler method of obtaining blood flow information of a patient by using the Doppler effect of an ultrasonic wave. In this technique, blood flow information of a patient is displayed as a Doppler spectral image defined by the blood flow velocity along the ordinate and the time along the abscissa. However, since the blood flow velocity changes depending on the measurement position and patient, it is necessary to adjust the measurement range (scale) of the blood flow velocity and a reference line (baseline) indicating a blood flow velocity of 0 in order to display the entire waveform. In the conventional technique, the operator presses an automatic adjustment button provided on the ultrasonic diagnostic apparatus to automatically adjust the scale and baseline, and display the entire waveform. In this technique, for example, the maximum amplitude of a waveform is estimated based on the maximum or minimum value of a blood flow velocity measured until the button is pressed, and the scale and baseline are adjusted.

However, in the conventional technique, the operator needs to take the trouble to press the automatic adjustment button, and this is cumbersome to the operator. When the operator wants to check the entire waveform soon and presses the automatic adjustment button before measuring the actual maximum and minimum values of the blood flow velocity, more specifically, before the lapse of the time of one heart beat, the scale and baseline are adjusted based on the maximum or minimum value of the blood flow velocity until he pressed the automatic adjustment button. As a result, the entire waveform may not be displayed.

BRIEF DESCRIPTION OF THE DRAWINGS

FIG. 2 is a flowchart according to the embodiment.
FIG. 3 is a graph showing a Doppler spectral image when no aliasing is generated.
FIG. 4 is a graph showing a Doppler spectral image when aliasing is generated.
FIG. 5 is graph showing a Doppler spectral image in which the baseline is adjusted.

DETAILED DESCRIPTION

Figure 1:
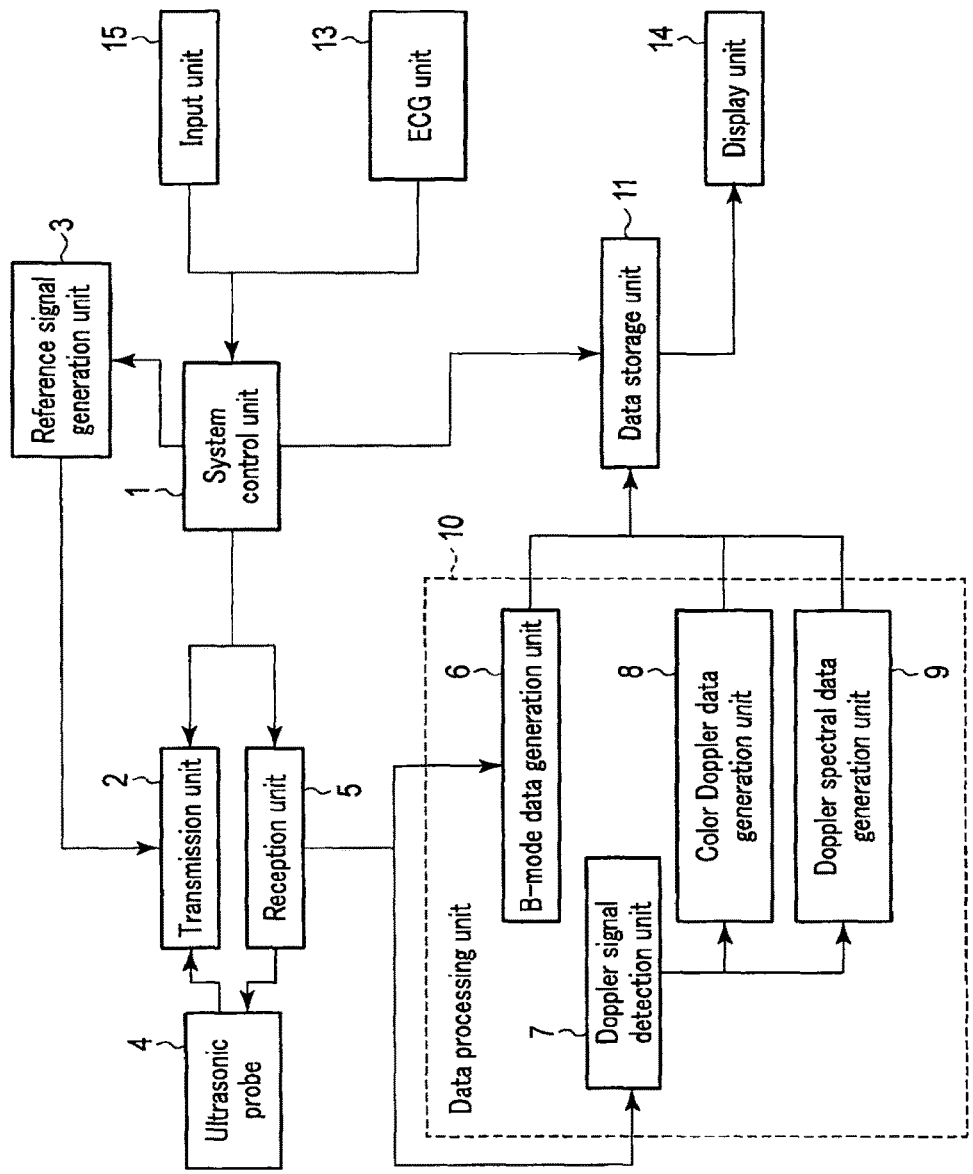
FIG. 1 is a block diagram according to an embodiment.

According to one embodiment, there is provided an ultrasonic diagnostic apparatus which comprises data processing circuitry, a display, input interface circuitry and system control circuitry. The data processing circuitry generates at least B-mode data and Doppler spectral data. The display displays images based on the B-mode data and the Doppler spectral data that have been generated by the data processing circuitry. The input interface circuitry inputs one of an instruction to transit to a mode of the Doppler spectral data and an operation to a range gate. The system control circuitry changes a display form of the Doppler spectral data displayed on the display based on the Doppler spectral data generated in a predetermined time after the input in response to the input to the input interface circuitry.

An embodiment of the present invention will now be described with reference to the accompanying drawings.

The arrangement of an ultrasonic diagnostic apparatus according to the embodiment will be explained with reference to the block diagram of FIG. 1.

The ultrasonic diagnostic apparatus according to this embodiment includes a system control unit 1, a transmission unit 2, a reference signal generation unit 3, an ultrasonic probe 4, a reception unit 5, a data processing unit 10, a data storage unit 11, an ECG (ElectroCardioGraph) unit 13, a display unit 14, and an input unit 15. The data processing unit 10 is realized processing circuitry and a memory, and includes a B-mode data generation unit 6, a Doppler signal detection unit 7, a color Doppler data generation unit 8, and a Doppler spectral data generation unit 9.

The system control unit 1 includes processing circuitry and a memory. When the operator instructs the system control unit 1 via the input unit 15 to generate B-mode data, the system control unit 1 creates control data for generating B-mode data and transfers, to the transmission unit 2, the created control data for generating B-mode data. In this case, the system control unit 1 instructs the reception unit 5 to supply an echo signal to the B-mode data generation unit.

When the operator instructs the system control unit 1 via the input unit 15 to generate color Doppler data, the system control unit 1 creates control data for generating color Doppler data and transfers, to the transmission unit 2, the created control data for generating color Doppler data. In this case, the system control unit 1 instructs the reception unit 5 to supply an echo signal to the Doppler signal detection unit 7, and instructs the Doppler signal detection unit 7 to supply a detected Doppler signal to the color Doppler data generation unit 8.

When the operator instructs the system control unit 1 via the input unit 15 to generate Doppler spectral data, the system control unit 1 creates control data for generating Doppler spectral data and transfers, to the transmission unit 2, the created control data for generating Doppler spectral data. In this case, the system control unit 1 instructs the reception unit 5 to supply an echo signal to the Doppler signal processing unit 7, and instructs the Doppler signal detection unit 7 to supply a detected Doppler signal to the Doppler spectral data generation unit 9. Note that this embodiment will explain a case in which Doppler spectral data is generated by performing sampling according to a pulsed Doppler method. However, a form in which sampling is performed according to a continuous wave Doppler method is also possible.

The system control unit 1 controls the display unit 14 to display an image (B-mode image) based on B-mode data stored in the data storage unit 11, an image (color Doppler image and color bar) based on color Doppler data stored in the data storage unit 11, and an image (Doppler spectral image) based on Doppler spectral data stored in the data storage unit 11.

The system control unit 1 sets the repetition frequency (Pulse Repetition Frequency: PRF) of a reference signal generated by the reference signal generation unit 3.

When generation of data transits in the order of B-mode data, color Doppler data, and Doppler spectral data or the order of B-mode data and Doppler spectral data, and "aliasing" is generated in a Doppler spectral image displayed on the display unit 14, the system control unit 1 instructs the reference signal generation unit 3 to set a PRF at which no aliasing is generated. Note that aliasing is aliasing of the frequency component of a Doppler signal based on the sampling theorem, and is generated when a Doppler signal has a frequency component larger than ½ of the magnitude of the PRF. Setting of a PRF at which no aliasing is generated will be described later.

The system control unit 1 controls the display unit 14 to display a predetermined input screen. The system control unit 1 also controls the display unit 14 to display a cursor and marker for designating a range in which color Doppler data is generated and a position at which Doppler spectral data is generated.

The reference signal generation unit 3 generates a reference signal at the timing based on the setting of the system control unit 1. In the following description, the time between generation of a reference signal at a given time point and generation of the next reference signal will be referred to as one rate.

The transmission unit 2 includes a memory (not shown) and stores, in the memory, control data received from the system control unit 1. When the reference signal generation unit 3 generates a reference signal to start the rate, the transmission unit 2 reads out control data regarding this rate from the memory, and supplies a driving pulse to the transducers of the ultrasonic probe 4 (to be described later) in accordance with the readout control data.

The ultrasonic probe 4 is, e.g., a linear ultrasonic probe including a plurality of transducers aligned one-dimensionally. Note that the ultrasonic probe 4 may be of the convex type and the sector type. Each transducer vibrates upon receiving a driving pulse from the transmission unit 2, and generates a transmission beam based on control data read out by the transmission unit 2. Each transducer receives a reflected wave generated upon reflection by the body tissue of a patient, and generates an echo signal. The ultrasonic probe 4 supplies each echo signal to the reception unit 5.

The reception unit 5 amplifies, by an amplifier (not shown), the signal strength of an echo signal supplied from the ultrasonic probe 4, and performs phasing addition processing based on control data. In accordance with an instruction from the system control unit 1, the reception unit 5 supplies the echo signal having undergone phasing addition processing to either the B-mode data generation unit 6 or the Doppler signal processing unit 7.

The B-mode data generation unit 6 performs processes such as envelope detection processing and logarithmic compression processing on an echo signal supplied from the reception unit 5 for each rate, thereby generating a reception signal corresponding to the amplitude intensity of the echo. The B-mode data generation unit 6 generates B-mode data based on the reception signal. The B-mode data generation unit 6 transmits the generated B-mode data to the data storage unit 11.

The Doppler signal detection unit 7 detects a Doppler signal from an echo signal supplied from the reception unit 5. When the operator instructs the system control unit 1 via the input unit 15 to generate color Doppler data, the Doppler signal detection unit 7 supplies the detected Doppler signal to the color Doppler data generation unit 8. In contrast, when the operator instructs the system control unit 1 via the input unit 15 to generate Doppler spectral data, the Doppler signal processing unit 7 supplies the detected Doppler signal to the Doppler spectral data generation unit 8.

The color Doppler data generation unit 8 generates color Doppler data based on a Doppler signal supplied from the Doppler signal detection unit 7. The color Doppler data is, e.g., data obtained by measuring the distribution of blood flow velocities in a range designated by the operator via the input unit 15 on the same slice as a B-mode image. The color Doppler data generation unit 8 transmits the generated color Doppler data to the data storage unit 11.

The Doppler spectral data generation unit 9 generates Doppler spectral data based on a Doppler signal supplied from the Doppler signal generation unit 7. The Doppler spectral data is, e.g., data obtained by measuring the time course of the blood flow velocity at a position designated by the operator via the input unit 15 on the slice of a B-mode image. The Doppler spectrum generation unit 9 transmits the generated Doppler spectral data to the data storage unit 11.

The data storage unit 11 includes, e.g., a storage means such as a hard disk (not shown), and stores B-mode data received from the B-mode data generation unit 6, color Doppler data received from the color Doppler generation unit 8, and Doppler spectral data received from the Doppler spectral data generation unit 9. The data storage unit 11 causes the display unit 14 to display the B-mode data, color Doppler data, and Doppler spectral data in accordance with an instruction from the system control unit 1.

The ECG unit 13 counts the heart beats of a patient, and sequentially notifies the system control unit 1 of the state of the heart beats.

The display unit 14 displays B-mode data, color Doppler data, and Doppler spectral data as images in accordance with an instruction from the system control unit 1. The display unit 14 displays a predetermined input screen in accordance with an instruction from the system control unit 1. Also, in accordance with an instruction from the system control unit 1, the display unit 14 displays a cursor and marker for designating a range in which color Doppler data is generated and a position at which Doppler spectral data is generated.

The input unit 15 includes, e.g., input interface circuitry such as a mouse and keyboard. The operator operates the cursor and marker displayed on the display unit 14 with the mouse and keyboard, and designates a range in which color Doppler data is generated and a position at which Doppler spectral data is generated.

Next, the operation of the ultrasonic diagnostic apparatus according to this embodiment will be explained with reference to the flowchart of FIG. 2.

In step S1, the operator starts diagnosis.

In step S2, the operator instructs the system control unit 1 via the input unit 15 to generate B-mode data. When the operator instructs the system control unit 1 via the input unit 15 to generate B-mode data, the system control unit 1 generates control data for generating B-mode data and transfers, to the transmission unit 2, the generated control data for generating B-mode data. The transmission unit 2 stores, in the memory, the control data for generating B-mode data, which has been transferred from the system control unit 1. After the memory stores all control data for generating B-mode data, the reference signal generation unit 3 generates a reference signal of a PRF set by the system control unit 1. If the reference signal generation unit 3 generates the reference signal to start the rate, the transmission unit 2 reads out control data regarding this rate from the memory, and supplies a driving pulse to the transducers of the ultrasonic probe 4 in accordance with the readout control data. Each transducer vibrates upon receiving the driving pulse from the transmission unit 2, and generates a transmission beam based on control data regarding this rate. Each transducer receives a reflected wave generated upon reflection by the body tissue of a patient, and generates an echo signal. The ultrasonic probe 4 supplies each echo signal to the reception unit 5. The system control unit 1 instructs the reception unit 5 to supply the echo signal to the B-mode data generation unit. The reception unit 5 amplifies, by the amplifier (not shown), the signal strength of the echo signal supplied from the ultrasonic probe 4, and performs phasing addition processing based on control data. In accordance with the instruction from the system control unit 1, the reception unit 5 supplies the echo signal having undergone phasing addition processing to the B-mode data generation unit 6. The B-mode data generation unit 6 performs processes such as envelope detection processing and logarithmic compression processing on the echo signal supplied from the reception unit 5, thereby generating a reception signal corresponding to the amplitude intensity of the echo. This process is executed till completion for all control data for generating B-mode data, which are stored in the memory of the transmission unit 2. The B-mode data generation unit 6 generates B-mode data based on all reception signals obtained here. The B-mode data generation unit 6 transmits the generated B-mode data to the data storage unit 11. The data storage unit 11 stores the B-mode data received from the B-mode data generation unit 6. The system control unit 1 controls the display unit 14 to display a B-mode image based on the B-mode data stored in the data storage unit 11. The display unit 14 displays the B-mode image.

In step S3, the operator designates, via the input unit 15, a range in which color Doppler data is generated from the B-mode image displayed on the display unit 14, and instructs the system control unit 1 to generate color Doppler data. When the operator instructs the system control unit 1 via the input unit 15 to generate color Doppler data, the system control unit 1 generates control data for generating color Doppler data and transfers, to the transmission unit 2, the generated control data for generating color Doppler data. The transmission unit 2 stores, in the memory, the control data for generating color Doppler data, which has been transferred from the system control unit 1. After the memory stores all control data for generating color Doppler data, the reference signal generation unit 3 generates a reference signal of a PRF set by the system control unit 1. If the reference signal generation unit 3 generates the reference signal to start the rate, the transmission unit 2 reads out control data regarding this rate from the memory, and supplies a driving pulse to the transducers of the ultrasonic probe 4 in accordance with the readout control data. Each transducer vibrates upon receiving the driving pulse from the transmission unit 2, and generates a transmission beam based on control data regarding this rate. Each transducer receives a reflected wave generated upon reflection by the body tissue of a patient, and generates an echo signal. The ultrasonic probe 4 supplies each echo signal to the reception unit 5. The reception unit 5 amplifies, by the amplifier (not shown), the signal strength of the echo signal supplied from the ultrasonic probe 4, and performs phasing addition processing based on control data. The system control unit 1 instructs the reception unit 5 to supply the echo signal to the Doppler signal detection 7. In accordance with the instruction from the system control unit 1, the reception unit 5 supplies the echo signal having undergone phasing addition processing to the Doppler signal processing unit 7. The Doppler signal detection unit 7 detects a Doppler signal from the echo signal supplied from the reception unit 5. Since the operator instructs the system control unit 1 via the input unit 15 to generate color Doppler data, the Doppler signal detection unit 7 supplies the detected Doppler signal to the color Doppler data generation unit 8. This process is executed till completion for all control data for generating color Doppler data, which are stored in the memory of the transmission unit 2. The color Doppler data generation unit 8 generates color Doppler data based on all reception signals obtained here. The color Doppler data generation unit 8 transmits the generated color Doppler data to the data storage unit 11. The data storage unit 11 stores the color Doppler data received from the color Doppler data generation unit 8. The system control unit 1 controls the display unit 14 to display a color Doppler image and color bar based on the color Doppler data stored in the data storage unit 11. The display unit 14 displays the color Doppler image and color bar.

In step S4, the operator designates, via the input unit 15, a position at which Doppler spectral data is generated from the B-mode image displayed on the display unit 14, and instructs the system control unit 1 to generate Doppler spectral data. Note that the position at which Doppler spectral data is generated is designated by, for example, moving the position of a range gate marker displayed on the display unit 14 by the operator via the input unit 15, and adjusting the range gate marker to the position at which Doppler spectral data is generated. When the operator instructs the system control unit 1 via the input unit 15 to generate Doppler spectral data, the system control unit 1 generates control data for generating Doppler spectral data regarding the designated position, and transfers, to the transmission unit 2, the generated control data for generating Doppler spectral data. The transmission unit 2 stores, in the memory, the control data for generating Doppler spectral data, which has been transferred from the system control unit 1. After the memory stores all control data for generating Doppler spectral data, the reference signal generation unit 3 generates a reference signal of a PRF set by the system control unit 1. If the reference signal generation unit 3 generates the reference signal to start the rate, the transmission unit 2 reads out control data regarding this rate from the memory, and supplies a driving pulse to the transducers of the ultrasonic probe 4 in accordance with the readout control data. Each transducer vibrates upon receiving the driving pulse from the transmission unit 2, and generates a transmission beam based on control data regarding this rate. Each transducer receives a reflected wave generated upon reflection by the body tissue of a patient, and generates an echo signal. The ultrasonic probe 4 supplies each echo signal to the reception unit 5. The reception unit 5 amplifies, by the amplifier (not shown), the signal strength of the echo signal supplied from the ultrasonic probe 4, and performs phasing addition processing based on control data. The system control unit 1 instructs the reception unit 5 to supply the echo signal to the Doppler signal detection 7. In accordance with the instruction from the system control unit 1, the reception unit 5 supplies the echo signal having undergone phasing addition processing to the Doppler signal processing unit 7. The Doppler signal detection unit 7 detects a Doppler signal from the echo signal supplied from the reception unit 5. Since the operator instructs the system control unit 1 via the input unit 15 to generate Doppler spectral data, the Doppler signal detection unit 7 supplies the detected Doppler signal to the Doppler spectral data generation unit 9.

This process is executed till completion for all control data for generating Doppler spectral data, which are stored in the memory of the transmission unit 2. The Doppler spectral data generation unit 9 generates Doppler spectral data based on all reception signals obtained here. The Doppler spectral data generation unit 9 transmits the generated Doppler spectral data to the data storage unit 11. The data storage unit 11 stores the Doppler spectral data received from the Doppler spectral data generation unit 9. The system control unit 1 controls the display unit 14 to display a Doppler spectral image based on the Doppler spectral data stored in the data storage unit 11. The display unit 14 displays the Doppler spectral data.

In step S5, the system control unit 1 confirms whether switching has passed through B-mode data. In other words, the system control unit 1 determines whether the generation of data has transited in the order of B-mode data, color Doppler data, and Doppler spectral data or the order of B-mode data and Doppler spectral data. If the generation of data has transited in the order of B-mode data, color Doppler data, and Doppler spectral data or the order of B-mode data and Doppler spectral data, the process shifts to step S6. If the generation of data has transited in neither the order of B-mode data, color Doppler data, and Doppler spectral data nor the order of B-mode data and Doppler spectral data, the process shifts to step S8.

In step S6, the system control unit 1 determines whether the scale of the Doppler spectral image displayed on the display unit 14 is proper. In this embodiment, the determination of whether the scale is proper is based on, for example, whether aliasing is generated in Doppler spectral data within the time of one heart beat counted by the ECG unit 13.

FIG. 3 is a graph showing a Doppler spectral image 101a and a baseline 102a when no aliasing is generated. FIG. 4 is a graph showing a Doppler spectral image 101b and a baseline 102b when aliasing is generated. As shown in FIG. 3, the maximum and minimum values of the blood flow velocity in the Doppler spectral data are observed repetitively in the cycle of a time T of one heart beat. This also applies to a case in which aliasing is generated. Hence, the determination of whether aliasing is generated only requires Doppler spectral data of at least one heart beat. As shown in FIGS. 3 and 4, whether aliasing is actually generated can be determined based on whether data in which a value near the maximum value of the scale abruptly changes to a value near the minimum value of the scale or a value near the minimum value of the scale abruptly changes to a value near the maximum value of the scale exists in Doppler spectral data of one heart beat. When there is data in which a value near the maximum value of the scale abruptly changes to a value near the minimum value of the scale or a value near the minimum value of the scale abruptly changes to a value near the maximum value of the scale, as described above, aliasing is generated in Doppler spectral data. For example, the system control unit 1 determines whether there is an amplitude level at which no Doppler spectral data exists in the period of one heart beat. If there is not an amplitude level at which no Doppler spectral data exists, for example, aliasing as shown in FIG. 4 is highly likely to occur in Doppler spectral data in this period of one heart beat. In this case, the system control unit 1 determines that aliasing is generated. If it is determined that there is an amplitude level at which no Doppler spectral data exists, for example, aliasing as shown in FIGS. 3 and 5 is highly likely not to occur in Doppler spectral data in this period of one heart beat. In this case, the system control unit 1 determines that no aliasing is generated. Note that such an aliasing determination method is described in detail in, e.g., Jpn. Pat. Appln. KOKAI Publication No. 8-308843.

If the system control unit 1 determines by the above-mentioned determination that aliasing is generated, that is, determines that the scale of the Doppler spectral image displayed on the display unit 14 is improper, the process shifts to step S7. To the contrary, if the system control unit 1 determines by the above-mentioned determination that no aliasing is generated, that is, determines that the scale of the Doppler spectral image displayed on the display unit 14 is proper, the process shifts to step S8.

In step S7, the system control unit 1 adjusts the scale. First, by using the Doppler spectral data in which aliasing is generated, the system control unit 1 estimates the maximum value (estimated maximum blood flow velocity) and minimum value (estimated minimum blood flow velocity) of the blood flow velocity on the assumption that the PRF is sufficiently high and no aliasing is generated. Based on the estimated maximum blood flow velocity and the estimated minimum blood flow velocity, the system control unit 1 sets the PRF of a reference signal to be generated by the reference signal generation unit 3. For example, the system control unit 1 adjusts the magnitude of the PRF so that the frequency component of a Doppler signal corresponding to a blood flow velocity of a velocity having a larger absolute value out of the estimated maximum blood flow velocity and the estimated minimum blood flow velocity becomes smaller than ½ of the magnitude of the PRF. After adjusting the magnitude of the PRF, the system control unit 1 starts generation of new Doppler spectral data as for the position designated in step S4. As in step S4, the system control unit 1 generates control data for generating new Doppler spectral data and transfers, to the transmission unit 2, the generated control data for generating new Doppler spectral data. The transmission unit 2 stores, in the memory, the control data for generating new Doppler spectral data, which has been transferred from the system control unit 1. After the memory stores all control data for generating new Doppler spectral data, the reference signal generation unit 3 generates a reference signal of a PRF set by the system control unit 1 in step S7. If the reference signal generation unit 3 generates the reference signal to start the rate, the transmission unit 2 reads out control data regarding this rate from the memory, and supplies a driving pulse to the transducers of the ultrasonic probe 4 in accordance with the readout control data. Each transducer vibrates upon receiving the driving pulse from the transmission unit 2, and generates a transmission beam based on control data regarding this rate. Each transducer receives a reflected wave generated upon reflection by the body tissue of a patient, and generates an echo signal. The ultrasonic probe 4 supplies each echo signal to the reception unit 5. The reception unit 5 amplifies, by the amplifier (not shown), the signal strength of the echo signal supplied from the ultrasonic probe 4, and performs phasing addition processing based on control data. The system control unit 1 instructs the reception unit 5 to supply the echo signal to the Doppler signal detection 7. In accordance with the instruction from the system control unit 1, the reception unit 5 supplies the echo signal having undergone phasing addition processing to the Doppler signal processing unit 7. The Doppler signal detection unit 7 detects a Doppler signal from the echo signal supplied from the reception unit 5. Since the operator instructs the system control unit 1 via the input unit 15 to generate Doppler spectral data, the Doppler signal detection unit 7 supplies the detected Doppler signal to the Doppler spectral data generation unit 9.

This process is executed till completion for all control data for generating new Doppler spectral data, which are stored in the memory of the transmission unit 2. The Doppler spectral data generation unit 9 generates new Doppler spectral data based on all reception signals obtained here. The Doppler spectral data generation unit 9 transmits the generated new Doppler spectral data to the data storage unit 11. The data storage unit 11 stores the new Doppler spectral data received from the Doppler spectral data generation unit 9. The system control unit 1 controls the display unit 14 to display a new Doppler spectral image based on the new Doppler spectral data stored in the data storage unit 11. The display unit 14 displays the new Doppler spectral image, and the process shifts to step S8. Note that the new Doppler spectral image displayed on the display unit 14 is an image displayed without aliasing in the entire waveform, as shown in FIG. 3.

In step S8, the operator continues the diagnosis by referring to the new Doppler spectral image for which the scale has been adjusted.

In step S9, for example, if the position of the ultrasonic probe 4 pressed against the patient shifts, or if the spatial position of the range gate is changed, the operator determines whether to generate Doppler spectral data again at almost the same measurement position. If the operator determines to generate Doppler spectral data again at almost the same measurement position, the process returns to step S3. If the process returns to step S3, the generation of data has transited in neither the order of B-mode data, color Doppler data, and Doppler spectral data nor the order of B-mode data and Doppler spectral data, adjustment of the scale by the system control unit 1 is not performed. Note that the adjustment of the scale is unnecessary because, even if the blood flow velocity is measured at almost the same measurement position, the maximum and minimum values of the blood flow velocity do not greatly change. If the operator determines not to generate Doppler spectral data again at almost the same position, the process shifts to step S10.

In step S10, the operator determines whether to generate Doppler spectral data by greatly changing the measurement position. If the operator determines to generate Doppler spectral data by greatly changing the measurement position, the process returns to step S2. In this case, the generation of data has transited in the order of B-mode data, color Doppler data, and Doppler spectral data or the order of B-mode data and Doppler spectral data. Thus, if the scale is improper in step S6, adjustment of the scale by the system control unit 1 is performed. Note that the adjustment of the scale is necessary because, if the measurement position is greatly changed, the maximum and minimum values of the blood flow velocity greatly change. If the operator determines not to generate Doppler spectral data by greatly changing the measurement position, the process shifts to step S11.

In step S11, the operator ends the diagnosis.

As described above, the ultrasonic diagnostic apparatus according to this embodiment causes the display unit to display an aliasing-free Doppler spectrum on a proper scale based on a blood flow velocity measured in the time of one heart beat without performing any operation by the operator. Since the operator need not press the button, unlike the conventional technique, the trouble of the operator is saved. The operator can obtain an aliasing-free Doppler spectrum on a proper scale by only waiting for the time of one heart beat. This prevents display of an improper waveform caused by pressing the button by the operator in haste when he wants to check the entire waveform soon, as in the conventional technique.

This embodiment has explained a case in which the scale is automatically adjusted based on a blood flow velocity measured in the time of one heart beat. However, the baseline may also be automatically adjusted in the same way, instead of or in addition to automatic adjustment of the scale.

FIG. 5 is a graph showing a Doppler spectral image 101c and a baseline 102c when they are properly displayed on the display unit 14 by adjusting the baseline. The case in which the baseline is proper is, for example, a case in which a difference L1 from the maximum value of the blood flow velocity to the upper limit value of the ordinate scale is equal to a difference L2 from the minimum value of the blood flow velocity to the lower limit value of the ordinate scale, as shown in FIG. 5. In order to automatically adjust the baseline in this manner, for example, the system control unit 1 obtains the maximum and minimum values of the blood flow velocity in Doppler spectral data in the time of one heart beat counted by the ECG unit 13 when the generation of data has been performed in the order of B-mode data, color Doppler data, and Doppler spectral data or the order of B-mode data and Doppler spectral data, and when no aliasing is generated in Doppler spectral data. Then, the system control unit 1 controls the display unit 14 to display a Doppler spectral image in a state in which the baseline is adjusted based on the maximum and minimum values so that L1 and L2 become equal to each other. Note that the magnitudes of L1 and L2 are preferably adjusted to be equal to or smaller than ½ of the difference between the upper and lower limit values of the scale of the ordinate displayed on the display unit 14. The waveform is therefore displayed at the center of the Doppler spectral image, so the operator can more easily observe the entire waveform. The automatic adjustment of the baseline is also applicable to, for example, a case in which an operation is performed on a display on which the waveform is folded on purpose at the top and bottom of a Doppler spectral image, in order to display the entire waveform even when the baseline exists at an improper position.

When a high PRF is set in advance not to cause aliasing, the entire waveform of a Doppler spectral image may be displayed by automatically adjusting the enlargement ratio/reduction ratio of the display of the Doppler spectral image on the display unit 14. In this case, the system control unit 1 obtains the maximum and minimum blood flow velocities of Doppler spectral data in the time of one heart beat counted by the ECG unit 13, enlarges or reduces the Doppler spectral image so as to have appropriate margins above and below the waveform, as shown in FIG. 5, and then displays the Doppler spectral image on the display unit 14. Since Doppler spectral data need not be newly generated, shortening of the diagnosis time can be expected.

Further, when respective data are generated in the order of color Doppler data and Doppler spectral data, the system control unit 1 may obtain the maximum and minimum values of the blood flow velocity in color Doppler data, perform adjustment of the scale, baseline, and reduction based on the maximum and minimum values, and control the display unit 14 to display the data. Note that the maximum and minimum values of the blood flow velocity here may be, e.g., the maximum and minimum values of color Doppler data at a position at which Doppler spectral data is generated, i.e., the position of the range gate marker, or may be maximum and minimum values obtained from color Doppler data at a plurality of positions around the position at which Doppler spectral data is generated. When generation of color Doppler data shifts to generation of Doppler spectral data, a Doppler spectral image of a proper display can be obtained from the beginning.

In addition to the automatic adjustment function of the scale and baseline described in the embodiment, automatic adjustment may be performed by pressing the automatic adjustment button by the operator, as in the conventional technique. Accordingly, a Doppler spectral image of operator's choice can be displayed.

The above-described embodiment has exemplified a case in which if it is determined in step S9 to generate Doppler spectral data at almost the same measurement position, the process returns to generation of color Doppler data in step S3 without adjusting the scale by the system control unit 1. However, the present embodiment is not limited to this example. For example, when it is determined in step S9 to generate Doppler spectral data at almost the same measurement position, even if the process transits to generation of B-mode data in step S2 and then transits from the B-mode to the color Doppler mode or the Doppler spectrum mode, adjustment of the scale by the system control unit 1 may not be performed. This arrangement is employed for the following reason. More specifically, for example, when the position of the ultrasonic probe or the position of the range gate slightly shifts during imaging in the Doppler spectrum mode, an operation of transiting to the B-mode to correct the shift, and then returning to the Doppler spectrum mode is sometimes performed. In such a case, the scale and the like need not be readjusted purposely because the user aims to correct the slightly shifted measurement position on the same blood vessel (that is, a blood vessel having almost the same flow velocity). With this arrangement, readjustment of the scale and the like need not be executed many times, and measurement processing can be performed comfortably. Note that whether to adopt this arrangement can also be selected by setting.

The above described "processing circuitry" means, for example, a central processing unit (CPU), a graphics processing unit (GPU), an application specific integrated circuit (ASIC), a programmable logical device (e.g., a simple programmable logic device (SPLD), a complex programmable logic device (CPLD), and a field programmable gate array (FPGA)), or the like.

Note that programs may be directly incorporated in processing circuitry instead that programs are stored in a memory 5m. In this case, the processing circuitry reads programs incorporated in circuitry and executes the programs to realize predetermined functions.

Each function (each component) in the present embodiment is not necessary to be corresponded to a single processing circuit and may be realized by a plurality of processing circuits. To the contrary, for example, at least two functions (at least two components) may be realized by a single processing circuit. Further, a plurality of functions (a plurality of components) may be realized by a single processing circuit.

Although embodiments of the present invention have been described above, they are presented as examples and are not intended to limit the scope of the invention. These novel embodiments can be implemented in other various forms, and various omissions, replacements, and changes can be made without departing from the scope of the present invention. These embodiments and their modifications are incorporated in the scope and spirit of the present invention, and are also incorporated in the scope of the invention and its equivalents defined in the appended claims.

The invention claimed is:

1. An ultrasonic diagnostic apparatus, comprising:
   data processing circuitry configured to generate at least B-mode data and Doppler spectral data;
   a display configured to display images based on the B-mode data and the Doppler spectral data generated by the data processing circuitry;
   input interface circuitry configured to input an instruction to transition to a Doppler spectral mode in which the Doppler spectral data is generate, and input an operation to set a range gate; and
   system control circuitry configured to
   determine, based on the Doppler spectral data generated in a predetermined time period after the input of the instruction to transition to the Doppler spectral mode is received, whether the generation of data has transited in an order of the B-mode data and the Doppler spectral data and whether aliasing was generated,
   change a display form of the Doppler spectral data displayed on the display when it is determined that both the generation of the data transits in the order of the B-mode data and the Doppler spectral data and that the aliasing was generated, does not change the display form of the Doppler spectral data displayed on the display when it is determined that the generation of the data does not transit in the order of the B-mode data and the Doppler spectral data or aliasing was not generated,
   wherein the predetermined time period starts upon transition to the Doppler spectral mode.

2. The ultrasonic diagnostic apparatus according to claim 1, wherein the data processing circuitry is further configured to generate color Doppler data,
   the input interface circuitry is further configured to input an instruction to transition to a color Doppler mode, and
   the system control circuitry further determines, based on the color Doppler data generated in the predetermined time internal after the input of the instruction to transition to the color Doppler mode is received, whether the generation of data has transited in an order of the B-mode data, the color Doppler data, and the Doppler spectral data and whether the aliasing was generated, changes the display form of the Doppler spectral data displayed on the display when it is determined that both the generation of the data transits in the order of the B-mode data, the color Doppler data, and the Doppler spectral data and that the aliasing was generated, and does not change the display form of the Doppler spectral data displayed on the display when it is determined that the generation of the data does not transit in the order of the B-mode data, the color Doppler data, and the Doppler spectral data.

3. The ultrasonic diagnostic apparatus according to claim 1, further comprising ECG circuitry configured to measure heart beats of a patient,
   wherein the predetermined time period is a time of at least one heart beat of the heart beats of the patient measured by the ECG circuitry.

4. The ultrasonic diagnostic apparatus according to claim 1, wherein the system control circuitry is further configured to change the display form of the image based on the Doppler spectral data displayed on the display by adjusting at least one of a scale, a baseline, an enlargement ratio, and a reduction ratio.

5. The ultrasonic diagnostic apparatus according to claim 1, wherein when a spatial position of one of an ultrasonic probe and the range gate is changed after changing the display form, the system control circuitry changes the display form of the Doppler spectral data displayed on the display in response to the change of the spatial position.

6. The ultrasonic diagnostic apparatus according to claim 1, wherein when the ultrasonic diagnostic apparatus transitions to a B-mode and then transitions to the Doppler spectral mode without an operation of the range gate after changing the display form, the system control circuitry does not change the display form of the Doppler spectral data displayed on the display.

* * * * *